(12) United States Patent
Johnson et al.

(10) Patent No.: US 9,289,324 B2
(45) Date of Patent: *Mar. 22, 2016

(54) EXTERNALLY ADJUSTABLE PASSIVE DRAINAGE DEVICE

(71) Applicant: ALCON RESEARCH, LTD., Fort Worth, TX (US)

(72) Inventors: Andrew David Johnson, Tustin, CA (US); Cesario Pereira Dos Santos, Aliso Viejo, CA (US); Casey Jean Lind, Orange, CA (US)

(73) Assignee: Novartis AG, Basel (CH)

( * ) Notice: Subject to any disclaimer, the term of this patent is extended or adjusted under 35 U.S.C. 154(b) by 348 days.

This patent is subject to a terminal disclaimer.

(21) Appl. No.: 13/975,870

(22) Filed: Aug. 26, 2013

(65) Prior Publication Data

US 2015/0057597 A1 Feb. 26, 2015

(51) Int. Cl.
*A61M 5/00* (2006.01)
*A61F 9/007* (2006.01)

(52) U.S. Cl.
CPC ..... *A61F 9/00781* (2013.01); *A61F 2250/0002* (2013.01)

(58) Field of Classification Search
CPC .......... A61F 9/00781; A61F 9/0017; A61F 9/00761; A61F 9/007; A61M 27/00; A61M 2210/0612; A61B 5/0084
USPC ............ 604/8, 9, 28; 606/107–108; 623/4.1, 623/1.12; 424/422, 423; 7/8, 9, 28
See application file for complete search history.

(56) References Cited

U.S. PATENT DOCUMENTS

| | | | |
|---|---|---|---|
| 4,089,329 A | 5/1978 | Couvillon, Jr. et al. |
| 4,206,762 A | 6/1980 | Cosman |
| 4,457,757 A | 7/1984 | Molteno |
| 4,560,375 A | 12/1985 | Schulte et al. |
| 4,656,827 A | 4/1987 | Puillet |
| 4,750,901 A | 6/1988 | Molteno |

(Continued)

FOREIGN PATENT DOCUMENTS

| | | |
|---|---|---|
| CN | 101360523 A | 2/2009 |
| CN | 101466299 A | 6/2009 |

(Continued)

OTHER PUBLICATIONS

Yasukawa T et al., 2001, "Biodegradable scleral plugs for vitreoretinal drug delivery", Adv. Drug Del Rev., 52(1), 25-36.

(Continued)

*Primary Examiner* — Philip R Wiest
(74) *Attorney, Agent, or Firm* — Kenneth D. Bassinger (57) ABSTRACT

Described herein is an IOP control device for implantation in an eye of a patient, comprising a housing including an inlet port and an outlet port, a fluid flow passageway configured to allow the flow of fluid from the inlet port to the outlet port, and at least one valve anchored within the housing. The at least one valve includes a first side and an opposing second side, and is configured to affect flow through the fluid flow passageway from the inlet port to the outlet port by moving in response to pressure differentials acting on the opposing first and second sides. The at least one valve is remotely adjustable between an active condition increasing resistance to the flow of fluid within the fluid flow passageway and an inactive condition decreasing resistance to the flow of fluid within the fluid flow passageway.

15 Claims, 5 Drawing Sheets

(56) References Cited

U.S. PATENT DOCUMENTS

| | | | |
|---|---|---|---|
| 4,869,282 A | 9/1989 | Sittler et al. |
| 4,922,913 A | 5/1990 | Waters, Jr. et al. |
| 5,005,577 A | 4/1991 | Frenkel |
| 5,083,742 A | 1/1992 | Wylie et al. |
| 5,178,604 A | 1/1993 | Baerveldt et al. |
| 5,179,953 A | 1/1993 | Kursar |
| 5,397,300 A | 3/1995 | Baerveldt et al. |
| 5,433,701 A * | 7/1995 | Rubinstein .......... A61F 9/00781 604/28 |
| 5,466,233 A | 11/1995 | Weiner et al. |
| 5,476,445 A | 12/1995 | Baerveldt et al. |
| 5,558,629 A | 9/1996 | Baerveldt et al. |
| 5,573,646 A | 11/1996 | Saito et al. |
| 5,626,558 A | 5/1997 | Suson |
| 5,681,275 A | 10/1997 | Ahmed |
| 5,707,643 A | 1/1998 | Ogura et al. |
| 5,910,110 A | 6/1999 | Bastable |
| 6,007,511 A | 12/1999 | Prywes |
| 6,048,328 A | 4/2000 | Haller et al. |
| 6,251,090 B1 | 6/2001 | Avery et al. |
| 6,447,449 B1 | 9/2002 | Fleischman et al. |
| 6,468,283 B1 | 10/2002 | Richter et al. |
| 6,579,235 B1 | 6/2003 | Abita et al. |
| 6,589,198 B1 | 7/2003 | Soltanpour et al. |
| 6,682,500 B2 | 1/2004 | Soltanpour et al. |
| 6,712,764 B2 | 3/2004 | Jeffries et al. |
| 6,719,750 B2 | 4/2004 | Varner et al. |
| 6,749,568 B2 | 6/2004 | Fleischman et al. |
| 6,939,299 B1 | 9/2005 | Petersen et al. |
| 6,976,982 B2 | 12/2005 | Santini, Jr. et al. |
| 7,137,952 B2 | 11/2006 | Leonardi et al. |
| 7,169,106 B2 | 1/2007 | Fleischman et al. |
| 7,252,006 B2 | 8/2007 | Tai et al. |
| 7,354,416 B2 | 4/2008 | Quiroz-Mercado et al. |
| 7,409,863 B2 | 8/2008 | Bateman et al. |
| 7,544,176 B2 | 6/2009 | Rodgers et al. |
| 7,612,328 B2 | 11/2009 | Kaiser |
| 7,756,559 B2 | 7/2010 | Abreu |
| 7,824,699 B2 | 11/2010 | Ralph et al. |
| 8,182,435 B2 | 5/2012 | Dacquay et al. |
| 8,206,440 B2 | 6/2012 | Guarnieri |
| 8,257,295 B2 | 9/2012 | Rickard et al. |
| 8,419,673 B2 | 4/2013 | Rickard |
| 2001/0000527 A1 | 4/2001 | Yaron et al. |
| 2002/0019607 A1 | 2/2002 | Bui |
| 2002/0049374 A1 | 4/2002 | Abreu |
| 2002/0087111 A1 | 7/2002 | Ethier et al. |
| 2002/0099359 A1 | 7/2002 | Santini, Jr. et al. |
| 2002/0139947 A1 | 10/2002 | Wang |
| 2002/0143284 A1 | 10/2002 | Tu et al. |
| 2002/0193674 A1 | 12/2002 | Fleischman et al. |
| 2003/0014036 A1 | 1/2003 | Varner et al. |
| 2003/0078487 A1 | 4/2003 | Jeffries et al. |
| 2003/0225318 A1 | 12/2003 | Montegrande et al. |
| 2004/0013702 A1 | 1/2004 | Glover |
| 2004/0059248 A1 | 3/2004 | Messner et al. |
| 2004/0073137 A1 | 4/2004 | Lloyd et al. |
| 2004/0111050 A1 | 6/2004 | Smedley et al. |
| 2004/0116794 A1 | 6/2004 | Fink et al. |
| 2004/0186367 A1 | 9/2004 | Fresco |
| 2004/0254438 A1 | 12/2004 | Chuck et al. |
| 2004/0254517 A1 | 12/2004 | Quiroz-Mercado et al. |
| 2005/0159660 A1 | 7/2005 | Montegrande et al. |
| 2005/0271704 A1 | 12/2005 | Tu et al. |
| 2005/0273033 A1 | 12/2005 | Grahn et al. |
| 2006/0131350 A1 | 6/2006 | Schechter et al. |
| 2007/0019156 A1 | 1/2007 | Fink |
| 2007/0032757 A1 | 2/2007 | Medow et al. |
| 2007/0077270 A1 | 4/2007 | Wen |
| 2007/0109117 A1 | 5/2007 | Heitzmann et al. |
| 2007/0123767 A1 | 5/2007 | Montegrande et al. |
| 2007/0129623 A1 | 6/2007 | Fleischman et al. |
| 2007/0212397 A1 | 9/2007 | Roth |
| 2008/0015421 A1 | 1/2008 | Penner |
| 2008/0027478 A1 | 1/2008 | Connors |
| 2008/0077127 A1 | 3/2008 | Gao et al. |
| 2008/0097276 A1 | 4/2008 | Bertrand et al. |
| 2008/0125691 A1 | 5/2008 | Yaron et al. |
| 2008/0129486 A1 | 6/2008 | Jeckelmann et al. |
| 2008/0147021 A1 | 6/2008 | Jani |
| 2008/0228127 A1 | 9/2008 | Burns et al. |
| 2009/0069648 A1 | 3/2009 | Irazoqui et al. |
| 2009/0076367 A1 | 3/2009 | Sit et al. |
| 2009/0143713 A1 | 6/2009 | Van Dam et al. |
| 2009/0227933 A1 | 9/2009 | Karageozian |
| 2009/0240215 A1 | 9/2009 | Humayun et al. |
| 2009/0275924 A1 | 11/2009 | Lattanzio et al. |
| 2009/0312742 A1 | 12/2009 | Pang et al. |
| 2010/0010416 A1 | 1/2010 | Juan, Jr. et al. |
| 2010/0042209 A1 | 2/2010 | Guarnieri |
| 2010/0121248 A1 | 5/2010 | Yu et al. |
| 2010/0174272 A1 | 7/2010 | Weiner |
| 2010/0222769 A1 | 9/2010 | Meng et al. |
| 2010/0234717 A1 | 9/2010 | Wismer |
| 2010/0253167 A1 | 10/2010 | Charnley et al. |
| 2010/0305550 A1 | 12/2010 | Meng et al. |
| 2011/0046536 A1 | 2/2011 | Stegmann et al. |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0248671 A1 | 10/2011 | Dos Santos et al. |
| 2013/0144202 A1 | 6/2013 | Field et al. |

FOREIGN PATENT DOCUMENTS

| | | |
|---|---|---|
| DE | 4438201 | 5/1996 |
| EP | 2427097 | 3/2012 |
| WO | 9303665 | 3/1993 |
| WO | 9803665 | 1/1998 |
| WO | 9803809 | 1/1998 |
| WO | 9938470 A2 | 8/1999 |
| WO | 9938470 A3 | 10/1999 |
| WO | 0194784 | 12/2001 |
| WO | 02056758 | 7/2002 |
| WO | 03001991 | 1/2003 |
| WO | 03102632 | 12/2003 |
| WO | 2005088417 | 9/2005 |
| WO | 2007127305 A2 | 11/2007 |
| WO | 2007136993 | 11/2007 |
| WO | 2008061043 A2 | 5/2008 |
| WO | 2008084350 | 7/2008 |
| WO | 2008061043 A3 | 9/2008 |
| WO | 2009010799 | 1/2009 |
| WO | 2009026499 | 2/2009 |
| WO | 2009049686 | 4/2009 |
| WO | 2009081031 | 7/2009 |
| WO | 2009081031 A3 | 9/2009 |
| WO | 2010129446 A1 | 11/2010 |
| WO | 2010136071 A1 | 12/2010 |
| WO | 2011034727 A1 | 3/2011 |
| WO | 2011034738 A1 | 3/2011 |
| WO | 2011034740 A1 | 3/2011 |
| WO | 2011034742 A2 | 3/2011 |
| WO | 2011035218 A1 | 3/2011 |
| WO | 2011034742 A3 | 5/2011 |
| WO | 2012012017 | 1/2012 |
| WO | 2013052332 A1 | 4/2013 |
| WO | 2013058943 A1 | 4/2013 |

OTHER PUBLICATIONS

Barton, Keith, et al., "The Ahmed Baerveldt Comparison Study," Journal of Ophthalmology, Jul. 15, 2010, vol. 118, No. 3, Elsevier, Inc., USA.

Byunghoon Bae, Hongseok Kee, Seonho Kim, Yeon Lee, Taeseok Sim, Yongkweon Him and Kyihwan Park; "In Vitro Experiment of the Pressure Regulating Valve for a Glaucoma Impact"; Journal of Micromechanics and Microengineering, 13 (2003); pp. 613-619.

Eggers, T., et al, "Wireless Intra-Ocular Pressure Monitoring System Integrated Into an Artificial Lens," 1st Annual Int'l IEEE-EMBS Special Topic Conference on Microtechnologies in Medicine & Biology, Oct. 12-14, 2000, pp. 166-469, Lyon, France.

(56) References Cited

OTHER PUBLICATIONS

Greene, M.E. and Gilman, B.G., "Intraocular Pressure Measurement With Instrumented Contact Lenses," Investigative Ophthalmology & Visual Science (IVOS), Apr. 1974, pp. 299-302, vol. 13, No. 4, IVOS.
Hjortdal, Jesper and Jensen, Peter, "In Vitro Measurement of Corneal Strain, Thickness, and Curvature Using Digital Image Processing," Acta Ophthalmologica Scandinavica, 1995, pp. 5-11, vol. 73, Denmark.
International Searching Authority, International Preliminary Report on Patentability, PCT/US2012/057261, May 1, 2014, 9 pages.
International Searching Authority, International Search Report of the International Searching Authority, PCT/US2010/047612, Dec. 21, 2010, 7 pages.
International Searching Authority, International Search Report, PCT/US2012/067747, Apr. 2, 2013, 4 pages.
International Searching Authority, International Search Report, PCT/US2012/068878, Mar. 3, 2013, 5 pages.
International Searching Authority, International Search Report, PCT/US2013/026066, Apr. 17, 2013, 5 pages.
International Searching Authority, Invitation to Pay Additional Fees and, Where Applicable, Protest Fee Partial Search Report attached), PCT/US2012/067741, Apr. 2, 2013, 6 pages.
International Searching Authority, Search Report and Written Opinion of the International Searching Authority, PCT/US2010/033329, Jul. 13, 2010, 15 pages.
International Searching Authority, Search Report and Written Opinion of the International Searching Authority, PCT/US2010/047429, Nov. 1, 2010, 15 pages.
International Searching Authority, Search Report and Written Opinion of the International Searching Authority, PCT/US2010/047600, Dec. 14, 2010, 13 pages.
International Searching Authority, Search Report and Written Opinion of the International Searching Authority, PCT/US2010/049424, Nov. 26, 2010, 15 pages.
International Searching Authority, Search Report of the International Searching Authority, PCT/US2011/036742, Aug. 17, 2011, 2 pages.
International Searching Authority, Search Report of the International Searching Authority, PCT/US2012/057261, Jan. 23, 2013, 7 pages.
International Searching Authority, Written Opinion of the International Searching Authority, PCT/US2010/047605, Dec. 16, 2010, 9 pages.
International Searching Authority, Written Opinion of the International Searching Authority, PCT/US2010/047612, Dec. 21, 2010, 10 pages.
International Searching Authority, Written Opinion of the International Searching Authority, PCT/US2012/057261, Jan. 23, 2013, 10 pages.
International Searching Authority, Written Opinion of the International Searching Authority, PCT/US2012/068878, Mar. 2, 2013, 8 pages.
International Searching Authority, Written Opinion of the International Searching Authority, PCT/US2013/026066, Apr. 17, 2013, 8 pages.
International Searching Authority, Written Opinion of the International Searcing Authority, PCT/US2012/067747, Apr. 2, 2013, 7 pages.
Kuppermann B D et al., 2006, "Efficacy and safety of a novel intravitreous dexamethasone drug-delivery system after applicator or incisional placement in patients with macular edema,", IOVS, 47 ARVO E-Abs 5913.
Lam, Andrew K.C. and Douthwaite, William A., "The Effect of an Artificially Intraocular Pressure on the Central Corneal Curvature," Ophthalmic and Physiological Optics, 1997, pp. 18-24, vol. 17, No. 1, Elsevier Science, Ltd., Great Britain.
Leonardi, Matteo, et al., "A Soft Contact Lens With a Mems Strain Gage Embedded for Intraocular Pressure Monitoring," In Proc. 12th Int'l Conference on Solid State Sensors, Actuators and Microsystems, Jun. 8-12, 2003, pp. 1043-1046, vol. 2, Boston, MA.

Leonardi, Matteo, et al., "First Steps Toward Noninvasive Intraocular Pressure Monitoring with a Sensing Contact Lens," Investigative Ophthalmology & Visual Science (IVOS), 2004, pp. 3113-3117, vol. 45, No. 9, IVOS.
VMcLaren, Jay W., et al, "Continuous Measurement of Intraocular Pressure in Rabbits by Telemetry," Investigative Ophthalmology & Visual Science (IVOS), May 1996, pp. 966-975, vol. 37, No. 6, IVOS.
Miyamoto H et al., 1997, Biodegradable scleral implant for intravitreal controlled release of fluconazole, Curr Eye Res, 16(9), 930-935.
Mokwa, Wilfried, et al, "Micro-Transponder Systems for Medical Applications," IEEE Transactions on Instrumentation and Measurement, Dec. 2001, pp. 1551-1555, vol. 50, No. 6, IEEE, Germany.
Mruthyunjaya P. et al., 2003, "An intravitreal sustained release fluocinolone acetonide device to treat severe experimental uveitis", IOVS, 44, ARVO E-Abs 4215.
Neagu Cristina R.; "A Medical Microactuator Based on an Electrochemical Principle"; Thesis at the Twente University,the Netherlands, Enschede; Aug. 28, 1998; pp. 1-162.
Nisar A., Afzulpurkar Nitin, Mahaisavariya Banchong, and Tuantranont Adisorn; "MEMS-Based Micropumps in Drug Delivery and Biomedical Applications"; ScienceDirect; Sensors and Actuators B 130 (2008) pp. 917-942.
Puers, Robert, "Linking Sensors with Telemetry: Impact on the System Design," In Proc. 8th Int'l Conference of Solid State Sensors, Actuators, Eurosens, Jun. 25-29, 1995, pp. 169-174, Stockholm, Sweden.
Ratanapakorn T et al., 2005, "Helical intravitreal triamcinolone implant: An explanation survival study", IVOS 46 E-Abs 484.
Rego MGR et al., 2004, "In vitro evaluation of sustained-release intravitreal dexamethasone implants", IOVS, 45 E-Abs 5060.
Sakurai E et al., 2001, "Scleral plug of biodegradable polymers containing ganciclovir for experimental cytomegalovirus retinitis", IOVS, 42(9), 2043-2048.
Saloomeh Saati MD., Ronalee Lo PhD, Po-Ying Li PhD, Ellis Meng PhD, Rohit Varma MD Mph, and Mark S. Humayun MD PhD; "Mini Drug Pump for Ophthalmic Use"; TRANS Am Ophthalmol Soc 2009; 107; pp. 50-71.
Schnakenberg, U., et al, "Initial Investigations on Systems for Measuring Intraocular Pressure," Sensors and Actuators, 2000, p. 287-291, vol. 85, Elsevier Science B.V., Germany.
See R F et al., 2006, "Safety and drug release profile of injectable intravitreal sustained-release fluocinolone acetonide device", IOVS, 47, ARVO E-Abs 5119.
Stangel, Karsten, et al, "A Programmable Intraocular CMOS Pressure Sensor System Implant," IEEE Journal of Solid-State Circuits, Jul. 2001, pp. 1094-1100, vol. 36, No. 7, IEEE, Germany.
Stemme, E. and Stemme, G.; "A Valveless Diffuser/Nozzle-Based Fluid Pump"; ScienceDirect; Sensors and Actuators A, 39 (1993); pp. 159-167.
Tano R et al., 2005, Helical intravitreal implant: surgical method development and outcomes, IOVS, 46, ARVO E-Abs 483.
Ullerich, Stella, et al, "Micro Coils for an Advanced System for Measuring Intraocular Pressure," 1st Annual Int'l IEEE-EMBS Special Topic Conference on Microtechnologies in Medicine & Biology, Oct. 12-14, 2000, pp. 470-474, Lyon, France.
Van Schuylenbergh, K., et al, "An Implantable Telemetric Tonometer for Direct Intraocular Pressure Measurements," 1st European Conference on Biomedical Engineering, Feb. 1991, pp. 194-195, vol. 17, No. 20, Nice, France.
Varner S E et al., 2003, "Development of a minimally invasive intravitreal implant for drug delivery", IOVS, 44, ARVO E-Abs 4214.
"Walter, Peter; Intraocular Pressure Sensor: Where Are We—Where Will We Go? Journal Graefe's Archive for Clinical and Experimental Ophthalmology; Publisher Springer Berline/Heidelberg; ISSN 0721-832X (Print) 1435-702X (Online); Issue vol. 240, No. 5/May, 2002 DOI 10.1007/s00417-002-0474-y; pp. 335-336; Subject collection Medicine."
Weiner A L, 2007, "Drug Delivery Systems in Ophthalmic Applications, In: Ocular Therapeutics; Eye on New Discoveries; T. Yorio, A. Clark, M.Wax, Eds, Elsevier Press/Academic Press, New York", pp. 7-43.

* cited by examiner

EXTERNALLY ADJUSTABLE PASSIVE DRAINAGE DEVICE

BACKGROUND

The present disclosure relates generally to valves and associated systems and methods. In some instances, embodiments of the present disclosure are configured to be part of an intraocular pressure (IOP) control system for use in ophthalmic treatments.

Glaucoma, a group of eye diseases affecting the retina and optic nerve, is one of the leading causes of blindness worldwide. Most forms of glaucoma result when the IOP increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

Figure 1:
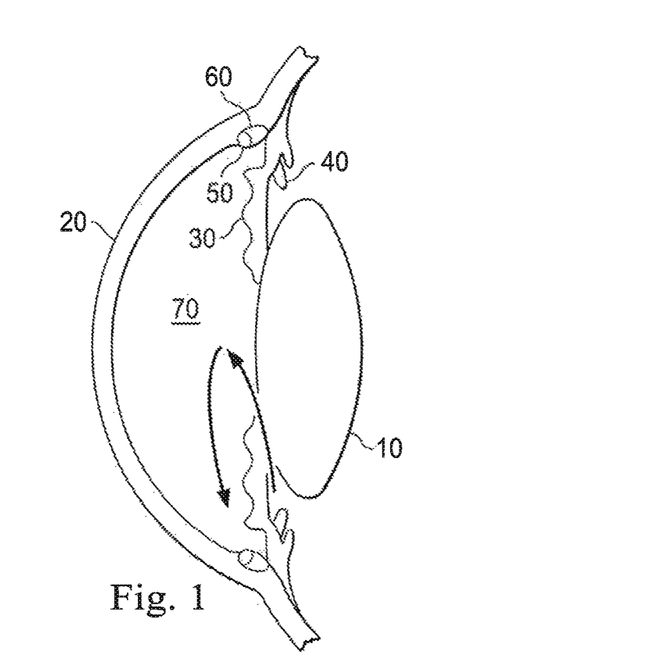
FIG. 1 is a diagram of the front portion of an eye.

FIG. 1 is a diagram of the front portion of an eye that helps to explain the processes of glaucoma. In FIG. 1, representations of the lens 10, cornea 20, iris 30, ciliary body 40, trabecular meshwork 50, and Schlemm's canal 60 are pictured. Anatomically, the anterior segment of the eye includes the structures that cause elevated IOP which may lead to glaucoma. The ciliary body 40 continuously produces aqueous humor, the clear fluid that fills the anterior segment of the eye (the space between the cornea and lens, or anterior chamber 70). The aqueous humor flows out of the anterior chamber 70 through the trabecular meshwork 50 into Schlemm's canal 60 and the uveoscleral pathways, both of which contribute to the aqueous humor drainage system. The trabecular meshwork may act as a filter, restricting the outflow of aqueous humor and generating a back pressure that directly relates to the IOP. The two arrows in the anterior segment of FIG. 1 show the flow of aqueous humor from the ciliary bodies 40, over the lens 10, over the iris 30, through the trabecular meshwork 50, and into Schlemm's canal 60 and its collector channels. The delicate balance between the production and drainage of aqueous humor determines the eye's IOP.

One method of treating glaucoma includes implanting a drainage device in a patient's eye. The drainage device allows fluid to flow from the anterior chamber of the eye to a drainage site, relieving pressure in the eye and thus lowering IOP. Once the drainage device is implanted, the body may form a bleb, or fluid-filled space surrounded by scar tissue, at the drainage site into which aqueous humor flows via a drainage tube. In order to provide desired treatments to patients, it may be important to regulate the flow of aqueous humor thorough the drainage device into the drainage site.

The system and methods disclosed herein overcome one or more of the deficiencies of the prior art.

SUMMARY

In one exemplary aspect, this disclosure is directed to an IOP control device for implantation in an eye of a patient comprising a housing, a fluid flow passageway, and at least one valve disposed within the housing. The housing is sized for implantation into the eye of the patient and includes an inlet port and an outlet port. The fluid flow passageway extends from the inlet port to the outlet port, and the passageway is configured to allow the flow of fluid from the inlet port to the outlet port. The at least one valve is disposed within the housing. In one aspect, the at least one valve includes a first side and an opposing second side, and is configured to affect flow through the fluid flow passageway from the inlet port to the outlet port by moving in response to pressure differentials acting on the opposing first and second sides. In one aspect, the at least one valve is remotely adjustable between an active condition increasing resistance to the flow of fluid within the fluid flow passageway and an inactive condition decreasing resistance to the flow of fluid within the fluid flow passageway.

In one aspect, the at least one valve comprises a switch element, and the switch element is movable between a first position and a second position relative to the housing, wherein the first position places the valve in the active condition and the second position places the valve in the inactive condition.

In one exemplary aspect, the present disclosure is directed to an IOP control system comprising a drainage device sized for implantation in an eye of a patient and an external control device. In one aspect, the drainage device comprises a drainage tube and a flow system in communication with the lumen of the drainage tube. In one aspect, the drainage tube includes a proximal end and a distal end and a lumen extending therebetween. In one aspect, the flow system comprises a housing, a fluid flow passageway, and a first valve disposed within the housing. The housing includes an inlet port and an outlet port. In one aspect, the fluid flow passageway extends from the inlet port to the outlet port, and is configured to allow the flow of fluid from the inlet port to the outlet port. In one aspect, the first valve is configured to have a first cracking pressure, a first side, and an opposing second side. In one aspect, the first valve is configured to affect flow through the fluid flow passageway by deflecting in response to pressure differentials acting on the opposing first and second sides. In one aspect, the external control device is operable to selectively and remotely control the first valve to assume an active condition wherein the first increases resistance to the flow of fluid within the fluid flow passageway and to assume an inactive condition wherein the first valve decreases resistance to the flow of fluid within the fluid flow passageway.

In another exemplary embodiment, the present disclosure is directed to a method of regulating drainage from an anterior chamber of an eye with an implantable device. The method comprises directing fluid through a housing defining a fluid flow passageway containing a flow system, the flow system comprising at least one valve. In one aspect, the method further comprises modifying the amount of drainage through the implantable device in response to an external control device acting on the at least one valve to selectively deactivate the at least one valve to decrease the resistance to fluid flow within the fluid flow passageway.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to a drainage system configured to regulate fluid flow by remotely adjusting pressure differential thresholds within a flow system inside a drainage device to allow flow through the drainage device. In some instances, embodiments of the present disclosure are configured to be used in the operation of valved drainage devices. In some instances, embodiments of the present disclosure are configured to be part of an IOP control system. Those of skill in the art will realize that the systems and devices disclosed herein may be utilized in alternative applications requiring the selective adjustment of pressure thresholds to allow and/or prevent the drainage of fluid.

Drainage devices which rely on the pressure differential between the anterior chamber and the drainage site may cause a detrimental hypotonous state by releasing aqueous humor too fast from the anterior chamber after the initial implantation. It is not until a few weeks after implantation that a bleb forms sufficiently to restrict the fluid flow and protect against hypotony. In addition, progressive scarring of the bleb over time may cause the bleb pressure to approach the anterior chamber pressure. This results in the pressure differential across the drainage device approaching zero as well. Devices that rely solely on the pressure differential between the anterior chamber and the drainage site to create flow through the device may eventually fail due to this effect.

The systems and devices disclosed herein allow a user to externally adjust the pressure threshold value necessary to open a drainage device in response to changes in the drainage site pressure over time. In particular, the systems and devices disclosed herein pertain to an external IOP control device and an implantable drainage device configured to extend from the anterior chamber of the eye to a drainage site.

Figure 2:
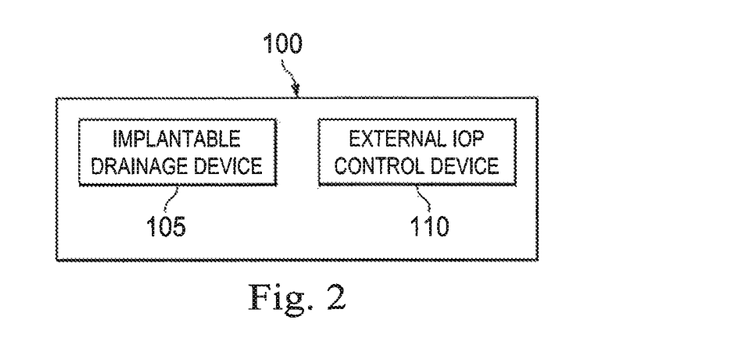
FIG. 2 is a block diagram of an exemplary IOP control system according to the principles of the present disclosure.

FIG. 2 is a schematic block diagram of an exemplary IOP control system 100 usable for the treatment of glaucoma or other ocular conditions according to the principles of the present disclosure. In FIG. 2, the IOP control system 100 comprises an implantable drainage device 105 and an external IOP control device 110. The drainage device 105 is designed to passively open when the pressure differential across a flow system (described with reference to FIG. 4) within the drainage device 105 exceeds a threshold value which may be adjusted by the external IOP control device 110. After a conventional pressure-driven passive drainage device is implanted within the eye, intraocular pressure tends to fall rapidly as aqueous fluid flows immediately through the drainage device to a drainage site. In the embodiments disclosed herein, the threshold setting of a series of valves forming the flow system (described with reference to FIG. 4) within the drainage device 105 can be remotely adjusted by a user using the external IOP control device 110. Thus, the systems and devices disclosed herein may extend the life of the drainage device 105 by allowing a user to externally adjust the pressure threshold of the flow system (described with reference to FIG. 4) to lower values as the drainage site pressure increases (e.g., as the bleb develops scar tissue). The drainage device 105 will be discussed further in relation to FIGS. 4, 5, and 7 below.

Figure 3:
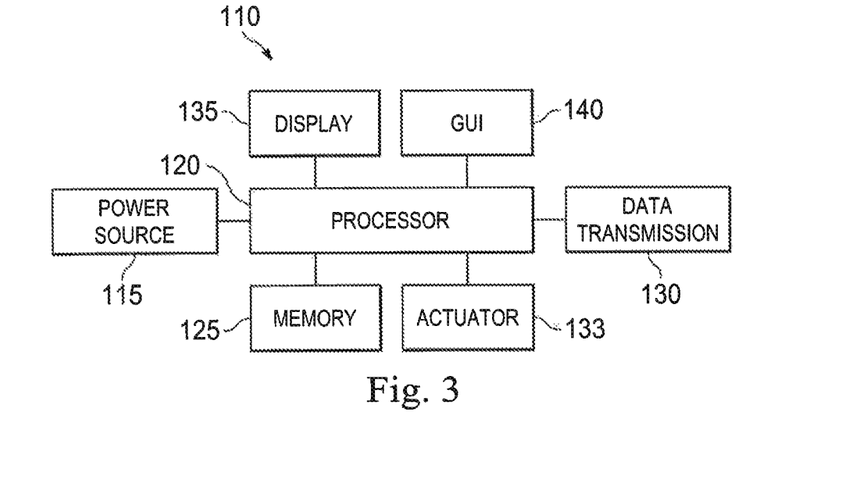
FIG. 3 is a block diagram of an exemplary external IOP control device according to the principles of the present disclosure.

FIG. 3 is a block diagram of the exemplary external IOP control device 110. The control device 110 can comprise any of a variety of devices, including, by way of non-limiting example, a personal digital assistant (PDA), a hand-held device, and a contact lens device configured for placement on the eye of the patient. In the pictured embodiment, the control device 110 comprises various component parts, including, by way of non-limiting example, a power source 115, a processor 120, a memory 125, a data transmission module 130, an actuator 133, a display 135, and a guided user interface (GUI) 140. The pictured component parts of the control device 110 are for illustrative purposes only, and are not intended to be limiting. In some embodiments, the control device 110 lacks some of these components. For example, in some embodiments, the control device 110 comprises only an actuator 133. In one embodiment, the control device 110 may be an external computing device configured to remotely actuate the opening and closing of individual valves within the drainage device 105.

The power source 115 is typically a rechargeable battery, such as a lithium ion or lithium polymer battery, although other types of batteries may be employed. In other embodiments, any other type of power cell is appropriate for the power source 115. The power source 115 provides power to the control device 110, and may provide power to the drainage device 105. In some examples, sufficient power is provided through on-board batteries and/or wireless powering. The power source 115 can be recharged via inductive coupling such as a radiofrequency (RF) link or other type of electromagnetic coupling. In some embodiments, the power source 115 may be an external supply of energy received through an electrical outlet.

The processor 120 is typically an integrated circuit with power, input, and output pins capable of performing logic functions. For example, the processor 120 may perform logic functions based on inputs from a user through the GUI 140. In some embodiments, the processor 120 controls the supply of power from the power source 115 to the drainage device 105 and/or signal commands to the drainage device 105. In various embodiments, the processor 120 may be a targeted device controller or a microprocessor configured to control more than one component of the device. The processor 120 may include one or more programmable processor units running programmable code instructions for implementing the pressure threshold modulation methods described herein, among other functions. The processor 120 may be integrated within a computer and/or other types of processor-based devices suitable for a variety of ocular applications. In various embodiments, the processor 120 can receive input data from the GUI 140, the drainage device 105, and/or various accessory devices via wireless or wired mechanisms. The processor 120 may use such input data to generate control signals to control or direct the operation of the drainage device 105. In some embodiments, the user can program or direct the operation of the drainage device 105 through the GUI 140. In some embodiments, the processor 120 is in direct wireless communication with the drainage device 105, and can receive data from and send commands to the drainage device 105.

The memory 125, which is typically a semiconductor memory such as random access memory (RAM), ferroelectric random access memory (FRAM), or flash memory, interfaces with the processor 120. As such, the processor 120 can write to and read from the memory 125, and perform other common functions associated with managing semiconductor memory. For example, a series of pressure readings and/or command sequences can be stored in the memory 125.

The processor 120 and/or the memory 125 may also include software containing one or more algorithms defining one or more functions or relationships between command signals and input data (received from either the GUI 140, the drainage device 105, and/or accessory devices). The algorithm may dictate activation or deactivation command protocols/signals depending on the received input data or mathematical derivatives thereof. The algorithm may dictate activation or deactivation control signals for particular valves on the implantable drainage device 105 (shown in FIG. 2) when the input data indicates an anterior chamber pressure below a predetermined threshold value, above a predetermined threshold value, or when the input data indicates a specific physiologic event, temporal state, or pathologic condition (e.g., hypotony, bleb scarring, or an initial post-operative state).

In various embodiments, the external IOP control device 110 may be operatively coupled to the drainage device 105 by way of wired or wireless communication mechanisms. In some embodiments, the external IOP control device 110 may affect the drainage device 105 by either (1) utilizing wireless communication between the drainage device 105 and the control device 110, or (2) utilizing trans-scleral or transdermal connections between the control device 110 and the drainage device 105. For example, the control device 110 may comprise a handheld programming device to operate and/or power the drainage device 105. Contemplated wireless communication methods include, by way of nonlimiting example, cooperating transmitters and receivers positioned on various components of the IOP control system 100 to allow remote communication between various components of the system 100 (shown in FIG. 2).

Thus, the data transmission module 130 may employ any of a number of different types of data transmission. For example, in various embodiments, the data transmission module 130 may be an active device such as a radio or a passive device with an antenna capable of wireless communication. In some embodiments, the data transmission module 130 may be activated to communicate the open and closed status of valves within the drainage device 105 to a secondary device such as a PDA, cell phone, computer, remote accessible data storage site (e.g. an internet server, email server, text message server), or other electronic device or service.

The actuator 133 can directly influence individual valves within the drainage device 105 to assume an open or closed position. The actuator 133 can selectively activate or deactivate individual valves of the flow system (described with reference to FIG. 4) independently of each other. In some embodiments, the actuator 133 comprises an electromagnet configured to selectively open and close individual valves within the drainage device 105. In some embodiments, the actuator 133 can act upon the drainage device 105 without the use of electronics or the processor 120. In other embodiments, the actuator 133 is controlled by the processor 120.

The GUI 140 may comprise any of a variety of input devices, including by way of non-limiting example, a keypad, a mouse, a joystick, dials, and buttons, among other input devices. In some embodiments, the GUI 140 and the display 135 comprise a single component. For example, in some embodiments, the display 135 comprises a liquid crystal display (LCD) with touch screen capability. In various embodiments, the display 135 may include any of a variety of display devices, including by way of non-limiting example, light-emitting diode (LED) displays, cathode ray tube (CRT) displays, and flat panel screens.

Figure 4:
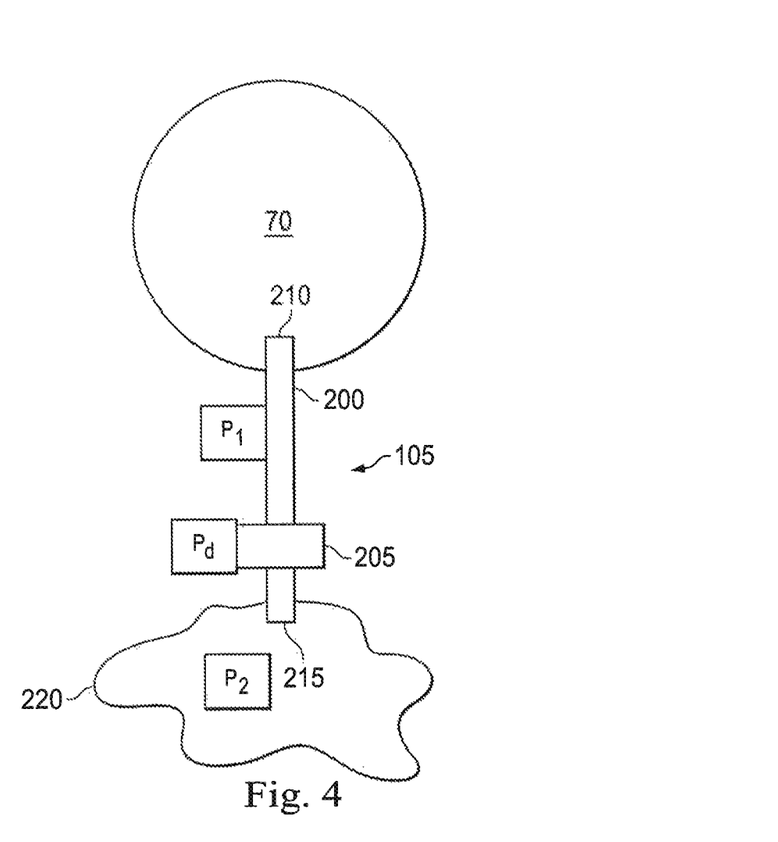
FIG. 4 is a schematic diagram of an exemplary IOP control system according to the principles of the present disclosure disposed within an eye.

FIG. 4 is a schematic diagram of the drainage device 105 implanted in an eye of a patient for the treatment of glaucoma or other ocular conditions. The drainage device 105 is configured in a manner that provides IOP pressure control in consideration of the patient's treatment stage and/or drainage site pressures, thereby reducing complications arising from surgical implant glaucoma treatments. In the embodiment pictured in FIG. 4, the drainage device 105 includes a drainage tube 200 and a flow system 205. The flow system 205 is disposed along, and may form a part of, the drainage tube 200 between a proximal end 210 of the drainage tube in the anterior chamber 70 and a distal end 215 of the drainage tube, which leads to a drainage site 220. The drainage tube 200 drains aqueous humor from the anterior chamber 70 of the eye to the drainage site 220. The flow system 205 controls the flow of aqueous humor through the drainage tube 200 and comprises one or more valves or other passive flow devices for regulating or otherwise affecting flow. For example, in one embodiment, the flow system 205 comprises a series of valves. In another embodiment, the flow system 205 of the drainage device 105 comprises a single valve.

In FIG. 4, the exemplary drainage device 105 includes at least two distinct pressure zones. The pressure zone P1 reflects the pressure of the anterior chamber 70, and the pressure zone P2 reflects the pressure of the drainage site 220. In some embodiments, the pressure zone P1 is located in a lumen or tube that is in fluid communication with the anterior chamber 70, such as the drainage tube 200. In the embodiment shown, the pressure zone P1 reflects the pressure in the tube 200 upstream from the flow system 205 and downstream from the anterior chamber 70. In this manner, pressure zone P1 reflects the pressure in the anterior chamber 70 because the expected measurement discrepancy between the true anterior chamber pressure and pressure within a tube downstream of the anterior chamber is very minimal.

The pressure zone P2 may be located in a pocket at the drainage site 220, such as a bleb, that generally contains aqueous humor. The drainage site 220 may be, by way of non-limiting example, in a subconjunctival space, a suprachoroidal space, a subscleral space, a supraciliary space, Schlemm's canal, a collector channel, an episcleral vein, and a uveo-scleral pathway, among other locations in the eye. The difference between the pressures at zones P1 and P2 (P1-P2) provides an indication of the pressure differential across the flow system 205 (i.e., between the anterior chamber 70 and the drainage site 220). In one embodiment, this pressure differential dictates the rate of aqueous humor flow from the anterior chamber 70 to the drainage site 220.

Pressure measurements from zones P1 and P2 can be entered into the system 100 by a user using the GUI 140 (shown in FIG. 3). Such pressure measurements may be stored in the memory 125 by the processor 120. They can later be read from the memory 125 so that the pressure differential over time can be interpreted by a user, such as a patient or a healthcare professional. In some embodiments, the pressure measurements may be visually depicted on the display 135 in any of a variety of forms, including, by way of non-limiting example, graphical and list forms.

The pressure value Pd reflects the overall pressure drop or cracking pressure across the flow system 205. The pressure value Pd reflects the cumulative pressure drops or cracking pressures of each individual valve within the drainage device 105.

The flow system 205 is configured to control the flow of drainage fluid through the drainage tube 200, and thereby affect pressure in the eye, including the IOP. A desired pressure differential (that corresponds to a desired flow rate) can be maintained by controlling the flow rate through the flow system 205. For example, when a measured pressure in zone P1 (i.e., anterior chamber pressure) is high, the flow system 205 may operate to permit increased flow through the drainage tube 200, and when a measured pressure in zone P1 is low, the flow system 205 may operate to decrease the flow through the drainage tube. Likewise, some embodiments of the flow system 205 are configured to control the flow of drainage fluid to the drainage site 220 (e.g., a bleb), and thereby control the bleb pressure to maintain a desired fluid flow to the bleb, decrease fibrosis, and increase absorption efficiency. To accomplish this, the flow system 205 may be responsive to command signals or instructions from the processor 215 of the external IOP control device 110 based on input data received from the GUI 140 and/or a pre-programmed treatment protocol (e.g., based on time lapse after initial implantation). Such a treatment protocol may be stored in the memory 125 (shown in FIG. 3). In some embodiments, the flow system 205 may be responsive to the actuator 133 of the external IOP control device 110 without the need for user input or processor instructions.

Figure 5:
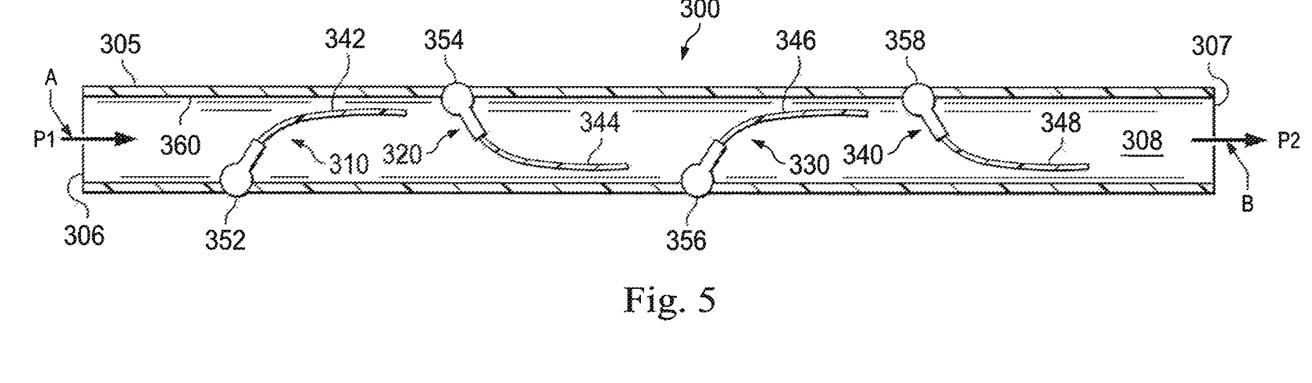
FIG. 5 is a stylized illustration of a cross-sectional view of an exemplary flow system according to the principles of the present disclosure, showing all the valves in an active condition.

FIG. 5 shows a stylized cross-sectional view of an exemplary flow system 300. The flow system 300 may be the same as the flow system 205 discussed with reference to FIG. 4. The flow system 300 is configured to selectively allow or block aqueous humor flowing from the anterior chamber 70 through the drainage tube 200 to the drainage site 220 (shown in FIG. 4) or to any subsequent flow control structures such as, by way of non-limiting example, valves, pumps, and/or check valves before entering the drainage site.

The flow system 300 comprises a housing 305 extending from an inlet port or inlet 306 to an outlet port or outlet 307. The housing 305 includes a fluid flow passageway 308 extending between the inlet 306 and the outlet 307. In the pictured embodiment, the flow system 300 includes four valves arranged in series: a first valve 310, a second valve 320, a third valve 330, and a fourth valve 340. Other embodiments may include any number and arrangement of valves. Each valve 310, 320, 330, 340 is configured as a flow control valve that can completely or partially block the flow of aqueous humor by deflecting a corresponding sealing portion 342, 344, 346, 348 completely or partially across the fluid flow passageway 308. In the pictured embodiment, the housing 305 is configured to connect with the drainage tube 200 (shown in FIG. 4) such that deflection of each sealing portion 342, 344, 346, 348 at least partially opens and closes the corresponding valve to the flow of aqueous humor.

The housing 305 comprises a hollow passageway allowing the passage of fluid. The housing 305 can be shaped in any of a variety of three-dimensional hollow shapes, including, by way of non-limiting example, a curved disc, an oblong plate, and a cylindrical tube. The housing 305 is arranged and configured relative to the drainage tube 200 to allow aqueous humor from the anterior chamber 70 to flow into the inlet 306, through the fluid flow passageway 308, past the valves 310, 320, 330, 340, and out the outlet 307 to the drainage site 220 (shown in FIG. 4). In particular, the inlet 306 may be in fluid communication with the drainage tube 200 and is configured to receive aqueous humor flowing from the drainage tube 200 into the fluid flow passageway 308. The outlet 307 permits fluid to exit the fluid flow passageway 308 for release at the drainage site 220. Thus, in the pictured embodiment, the pressure zone P1 is located proximal to the inlet 306 and the pressure zone P2 is located distal to the outlet 307. The fluid flow through the flow system 205 is dependent upon the pressure differential between the pressure zone P1 at the inlet 306 and the pressure zone P2 at the outlet 307 (corresponding to the pressure zones P1 and P2 shown in FIG. 4).

In the pictured embodiment, the valves 310, 320, 330, 340 are shaped and configured as cantilever valves that permit fluid flow in the direction of arrows A and B from the inlet 306 to the outlet 307. Each valve 310, 320, 330, 340 includes the corresponding sealing portion 342, 344, 346, 348, respectively, coupled to a switch element 352, 354, 356, 358, respectively. The valves 310, 320, 330, 340 and an inner surface 360 of the housing 305 are shaped and configured such that deflection of each respective sealing portion 342, 344, 346, 348 at least partially opens and closes the each valve to the outflow of aqueous humor from the flow system 300. Regardless of how each switch element 352, 354, 356, 358 is secured within the housing 305, at least a portion of the housing 305 is coupled to a section of the switch element to maintain its respective sealing portion 342, 344, 346, 348 in a desired position relative to the inner surface 360. The inner surface 360 provides the valve seat against which the sealing portions 342, 344, 346, 348 may rest to close their respective valves. The inner surface 360 is shaped and configured such that when the sealing portion 342, 344, 346, 348 rests on the inner surface 360, the corresponding valve 310, 320, 330, 340 is in a closed condition. In the pictured embodiment, the valves 310, 320, 330, 340 are each substantially identical to one another. In other embodiments, the valves 310, 320, 330, 340 may be shaped and configured differently from one another, provided that each valve is capable of selectively restricting the flow of fluid through the fluid flow passageway 308 based on the pressure differential between the pressure zones P1 and P2.

The sealing portion 342, 344, 346, 348 may be formed of an elastically deformable biocompatible material such as, by way of non-limiting example, silicone, silicon nitride, silicone elastomer, polyimide, Parylene, and others. In the example shown, the sealing portion 342, 344, 346, 348 is a substantially planar membrane secured at its periphery to its respective switch element 352, 354, 356, 358. Each sealing portion 342, 344, 346, 348 comprises a flexible membrane responsive to a pressure differential across a first membrane surface and an opposing second membrane surface. For purposes of practicality, the sealing portion 342, 344, 346, 348 should be thick enough to be durable and resistant to corrosion and leakage. However, the sealing portion 342, 344, 346, 348 should also be thin enough to provide the necessary flexibility and deflection capabilities which are required in a substantially planar membrane designed for use in a pressure-responsive control system. A preferred thickness of the sealing portion 342, 344, 346, 348 will depend on the deflection response desired for a given pressure and the material chosen. As an example, the sealing portion 342 may be fabricated out of Parylene and may have a thickness ranging from 0.5 µm to 30 µm. The sealing portion 344 may have a similar thickness and material as the sealing portion 342, or for the sake of illustrating a different choice, it could be made of silicon and have a thickness ranging from 0.3 µm to 10 µm. In some embodiments, the membranes are substantially flat, without corrugation features. In some embodiments, any number of the sealing portions 342, 344, 346, 348 may include indentations or corrugations whose depths affect the deflection profile of the sealing portion in response to various pressures. The thickness, material, and diameter of the sealing portions 342, 344, 346, 348, as well as the depth, number, and orientation of the corrugations, may all affect the cracking pressure and deflection profiles of the sealing portions 342, 344, 346, 348.

The cracking pressure of a valve generally refers to the minimum pressure differential needed between the entrance and exit of the valve to lift the sealing portion off its valve seat, thereby allowing the valve to assume an open condition allowing fluid flow past the valve. The cracking pressure of each valve 310, 320, 330, 340 is dependent upon the structure and configuration of the valve itself. If the cracking pressure of the valve 310, 320, 330, 340 is high in comparison to the pressure differential across the valve, the sealing portion 342, 344, 346, 348, respectively, will remain in contact with the inner surface 360, which prevents flow through the valve. When the sealing portion 342, 344, 346, 348 rests on the inner surface 360, the sealing portion prevents the flow of fluid through the fluid flow passageway 308 toward the outlet 307, and the corresponding valve 310, 320, 330, 340, respectively, is in a closed position.

If the pressure differential across the valve 310, 320, 330, 340 overcomes or is greater than the cracking pressure of the valve, the corresponding sealing portion 342, 344, 346, 348, deflects away from the inner surface 360. When the sealing portion 342, 344, 346, 348 lifts away from the inner surface 360, the corresponding valve 310, 320, 330, 340 is in an open condition and fluid in the fluid flow passageway 308 may flow past the corresponding valve toward the outlet 307. Thus, the flow of aqueous humor through the flow system 300 to the outlet 307 (and ultimately the drainage site 220) depends at least in part upon the pressure differential across the flow system (i.e., pressure in zone P1 relative to the pressure in zone P2) and the cracking pressure of the individual valves 310, 320, 330, 340.

The cracking pressure of a valve is dependent on the structural characteristics of the valve and the valve seat. Therefore, the cracking pressure of the valves 310, 320, 330, and 340 may be dependent upon the geometry (e.g., size and shape) and material characteristics (such as stiffness) of the switch elements 352, 354, 356, 358 and sealing portions 342, 344, 346, 348, as well as the coupling mechanism of the switch elements to the housing 305. For example, the specific configuration and structure of the flow system 300 can be selected to create a particular cracking pressure for the valves 310, 320, 330, and 340. Accordingly, the cracking pressure of valves 310, 320, 330, and 340 may be preselected by controlling these parameters during the manufacturing or assembly processes. In addition, the healthcare provider may select the particular flow system 305 including valves having particular cracking pressures based on the most appropriate or desired IOP range for the treatment of a particular condition.

The IOP control system 100 shown in FIG. 2 may be used to address complications associated with underfiltration of aqueous humor from the anterior chamber 70 (shown in FIGS. 1 and 4). For example, one complication associated with implantation of glaucoma drainage devices is the development of a fluid-filled bleb at the drainage site 220 shown in FIG. 4. The development of the bleb typically leads to scarring and fibrosis at the drainage site 220, which may lead to increased flow resistance through the drainage device 105. Generally, this resistance increases over time as the development and progression of fibrosis reduces or eliminates flow from the anterior chamber 70, eliminating the capacity of the drainage device 105 to affect IOP.

While various complications may arise from elevated IOP, other complications may arise from excessively low IOP as well. For example, another complication associated with implantation of glaucoma drainage devices is hypotony, which is described above as a rapid drop in IOP that can result in severe consequences such as choroidal hemorrhage and choroidal detachment. Thus, it is desirable to control the rate of aqueous outflow from the anterior chamber 70 to the drainage site 220 (shown in FIG. 4) not only to prevent underfiltration of aqueous humor from the anterior chamber 70, but also to prevent overfiltration and hypotony.

In one embodiment, the IOP control system 100 (as shown in FIG. 2), comprising the implantable drainage device 105 and the external IOP control device 110, is configured to affect IOP by adjusting the flow through the flow system 300 in response to commands from a user (utilizing measured pressure values). In particular, the flow system 300 within the drainage device 105 is configured to respond to the external IOP control device 110 to control the flow rate through the drainage tube 200. Each valve 310, 320, 330, 340 within the flow system 300 will assume an open condition when the fluid pressure differential across the valve surpasses a threshold cracking pressure of the valve. Thus, increasing the cracking pressure of a particular valve 310, 320, 330, 340 increases the pressure threshold needed for that valve to assume an open condition and allow fluid flow past that valve. Similarly, decreasing the cracking pressure of a particular valve 310, 320, 330, 340 decreases the pressure threshold needed for a valve to assume an open condition.

In an exemplary scenario, a healthcare provider can measure the pressure within the anterior chamber (i.e., pressure within pressure zone P1) and determine whether the aqueous humor is draining from the anterior chamber in a desirable fashion. As time passes after the initial implantation of the drainage device 105, the initial pressure threshold of the flow system 300 may not be ideal. If the measured anterior chamber pressure indicates that aqueous flow is occurring in an appropriate fashion, then no adjustment may be needed. If, however, the healthcare provider determines that the aqueous humor is not draining appropriately from the eye (e.g., if the anterior chamber pressure is not within a desired range), the healthcare provider may then increase or decrease the pressure threshold of the flow system 300 using the external IOP control device 110, thereby decreasing or increasing, respectively, the aqueous flow from the anterior chamber through the drainage device 105 to effect a pressure change to the desired anterior chamber pressure. To do this, the user can use the external IOP control device 110 to adjust the flow system 300 by wirelessly activating or deactivating individual switch elements 352, 354, 356, 358, thereby changing the pressure drop across the drainage device 105.

As shown in FIG. 5, each switch element 352, 354, 356, 358 is attached to the housing 305 in such a manner as to enable the switch element to move between at least two positions within the fluid flow passageway 308. In particular, each switch element 352, 354, 356, 358 is movable between an ACTIVE position providing resistance to the path of fluid flowing past the valves 310, 320, 330, 340, respectively, and an INACTIVE position allowing fluid to flow freely past the valves 310, 320, 330, 340, respectively. In the pictured embodiment, the switch elements 352, 354, 356, 358 are bi-stable, meaning that the switch elements remain in one of the ACTIVE or INACTIVE positions until controlled by the external IOP control device 110 to assume the other position. In FIG. 5, each switch element 352, 354, 356, 358 is in an ACTIVE position, thereby placing each sealing portion 342, 344, 346, 348, respectively, into the fluid flow passageway 308. When the switch element 352, 354, 356, 358 is in the ACTIVE position, its respective sealing portion 342, 344, 346, 348 moves away from the inner surface 360 of the housing 305 into the fluid flow passageway 308, thereby providing resistance to the flow of fluid past the valve (i.e., thereby increasing the cracking pressure of the corresponding valve and contributing to the overall pressure drop across the flow system 300). In the situation depicted in FIG. 5, fluid may flow passively through the flow system 300 if the pressure differential P1:P2 overcomes the sum of the cracking pressures across the flow system (i.e., the combined cracking pressures of the valves 310, 320, 330, and 340).

Figure 6:
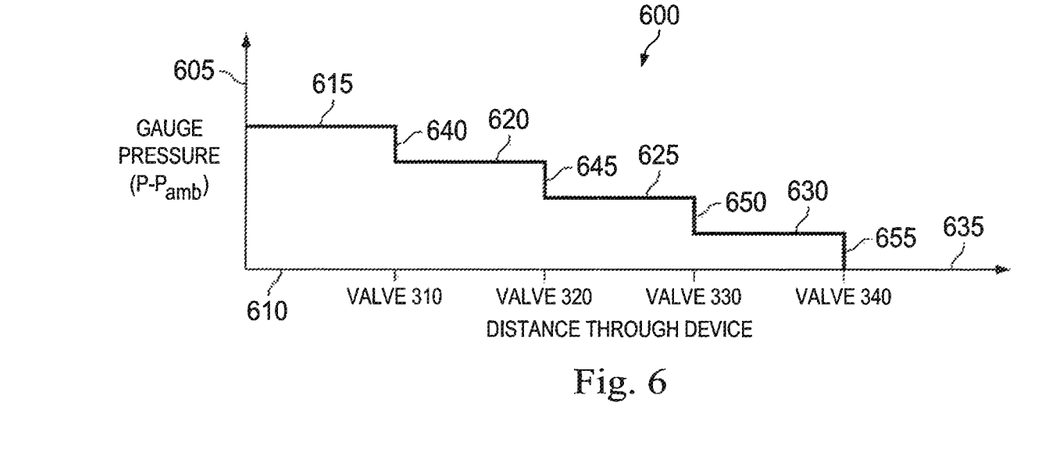
FIG. 6 is a graphical illustration of changes in gauge pressure within and along the length of the exemplary flow system as depicted in FIG. 5, where all the valves are in an active condition.

FIG. 6 illustrates a graph 600 depicting the changes in gauge pressure within and along the length of the drainage device 105 in a situation where each valve 310, 320, 330, and 340 is in an active condition (i.e., contributing to the pressure drop across the drainage device 105). The y-axis 605 of the graph in FIG. 6 reflects the gauge pressure (absolute pressure within the drainage tube 200 minus the ambient pressure), and the x-axis 610 reflects the position within the length of the drainage device 105 past the valves 310, 320, 330, and 340 (i.e., the distance travelled by the fluid within the drainage device 105).

In one exemplary situation, the graph 600 depicts the pressure changes along the length of the drainage device 105 in the initial post-operative stage after implantation of the drainage device 105 into a patient's eye. In the initial post-operative stage, the drainage device 105 can be preset or programmed (using the external IOP control device 110) to have each switch element 352, 354, 356, 358 is in an ACTIVE position (as shown in FIG. 5). When each switch element 352, 354, 356, 358 is in an ACTIVE position, each corresponding valve 310, 320, 330, and 340 contributes to the pressure drop across the drainage device 105. In other words, when each switch element 352, 354, 356, 358 is in an ACTIVE position, each corresponding valve 310, 320, 330, and 340 adds to the threshold pressure necessary to be overcome to allow fluid to drain through the drainage device 105. Thus, when each switch element 352, 354, 356, 358 is in an ACTIVE position, the drainage device 105 has the maximum pressure threshold needed to be overcome to allow fluid to flow through the drainage device 105 to the outlet 307 (shown in FIG. 5). This scenario may aid in preventing hypotony secondary to the overly rapid filtration of aqueous humor through the drainage device 105.

Line 615 represents the gauge pressure within the drainage device 105 proximal of the valve 310. In the pictured embodiment, line 615 reflects the pressure within the drainage device 105 at zone P1 (shown in FIG. 4), or the anterior chamber pressure. In the pictured embodiment, line 620 reflects the pressure within the drainage device 105 between the valve 310 and the valve 320. In the pictured embodiment, line 625 reflects the pressure within the drainage device 105 between the valve 320 and the valve 330. In the pictured embodiment, line 630 reflects the pressure within the drainage device 105 between the valve 330 and the valve 340. In the pictured embodiment, line 635 reflects the pressure within the drainage device 105 distal to the valve 340 (e.g., at the drainage site 220 shown in FIG. 4). In the pictured situation, the pressure at the drainage site 220 (depicted by line 635) is approximately 0 mmHg.

As shown by the graph 600, the pressure within the drainage device 105 decreases in a staggered or stepwise fashion by discrete amounts reflecting the pressure drops across the series of valves 310, 320, 330, and 340. Line 640 represents the pressure drop across the valve 310. Line 645 represents the pressure drop across the valve 320. Line 650 represents the pressure drop across the valve 330. Line 655 represents the pressure drop across the valve 340. In the pictured embodiment, each valve 310, 320, 330, and 340 has the same pressure drop. For example, in one embodiment, the valves 310, 320, 330, and 340 may each have a pressure drop of 3 mmHg (i.e., each valve may contribute 3 mmHg to the overall threshold pressure threshold needed to be overcome by the fluid to flow through the drainage device 105). In other embodiments, the valves 310, 320, 330, and 340 may have different pressure drops from one another. For example, in one embodiment, the valve 310 may have a pressure drop of 1 mmHg, the valve 320 may have a pressure drop of 2 mmHg, the valve 330 may have a pressure drop of 3 mmHg, and the valve 340 may have a pressure drop of 4 mmHg. In another embodiment, the valve 310 may have a pressure drop of 4 mmHg, the valve 320 may have a pressure drop of 4 mmHg, the valve 330 may have a pressure drop of 2 mmHg, and the valve 340 may have a pressure drop of 2 mmHg. Depending upon the application, the valves within the drainage device 105 may have the same or different pressure drops across each valve, and the valves may be arranged in any order within the drainage device 105.

Figure 7:
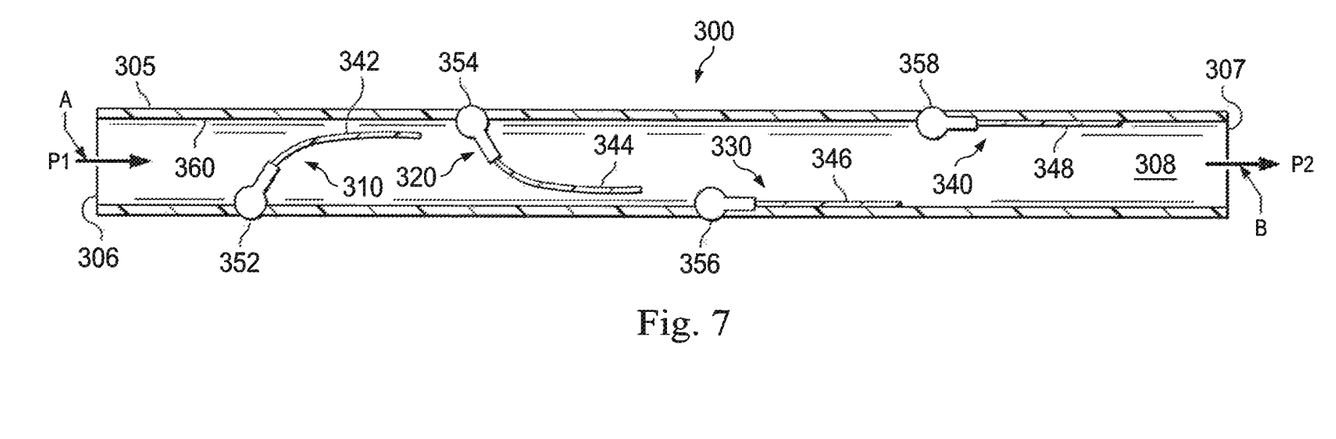
FIG. 7 is a stylized illustration of a cross-sectional view of the exemplary flow system shown in FIG. 5, showing some valves in an inactive condition and other valves in an active condition.

During the stage of progressive bleb scarring (or any other condition that increases the pressure within zone P2 at the drainage site 220 shown in FIG. 4), the external IOP control device 110 (shown in FIGS. 2 and 3) can be used to direct one or more switch elements to assume an INACTIVE position through wired or wireless communication with the drainage device 105, as described above. For example, FIG. 7 shows a stylized cross-sectional view of an exemplary flow system 300 when the switch elements 352, 354 are in an ACTIVE condition and the switch elements 356, 358 are in the INACTIVE condition. When any individual switch element 352, 354, 356, 358 is in the INACTIVE position, it moves toward the inner surface 360 of the housing 305 and its respective sealing portion 342, 344, 346, 348 flattens against the inner surface 360 near where the switch element is attached to the housing 305, thereby decreasing the resistance to the flow of fluid past its respective valve 310, 320, 330, 340 and diminishing the pressure drop across the valve. In particular, in FIG. 7, the valves 310 and 320 are contributing to the pressure drop across the flow system 300 and the valves 330 and 340 are not. The switch elements 352, 354 are in ACTIVE positions and the respective sealing portions 342, 344 are providing resistance to the flow of fluid past the valves 310, 320, respectively, and increasing the overall resistance across the flow system 300. Increasing the overall resistance across the flow system 300 increases the fluid pressure differential (i.e., the pressure differential between zones P1 and P2) necessary to allow fluid to passively traverse and exit the flow system 300. In contrast, the switch elements 356, 358 are in INACTIVE positions and the respective sealing portions 346, 348 are positioned substantially flush against the inner surface 360 of the housing 305, thereby diminishing the resistance to the flow of fluid past the valves 330, 340 and decreasing the overall resistance across the flow system 300. Decreasing the overall resistance across the flow system 300 decreases the fluid pressure differential necessary to allow fluid to passively traverse and exit the flow system 300.

Figure 8:
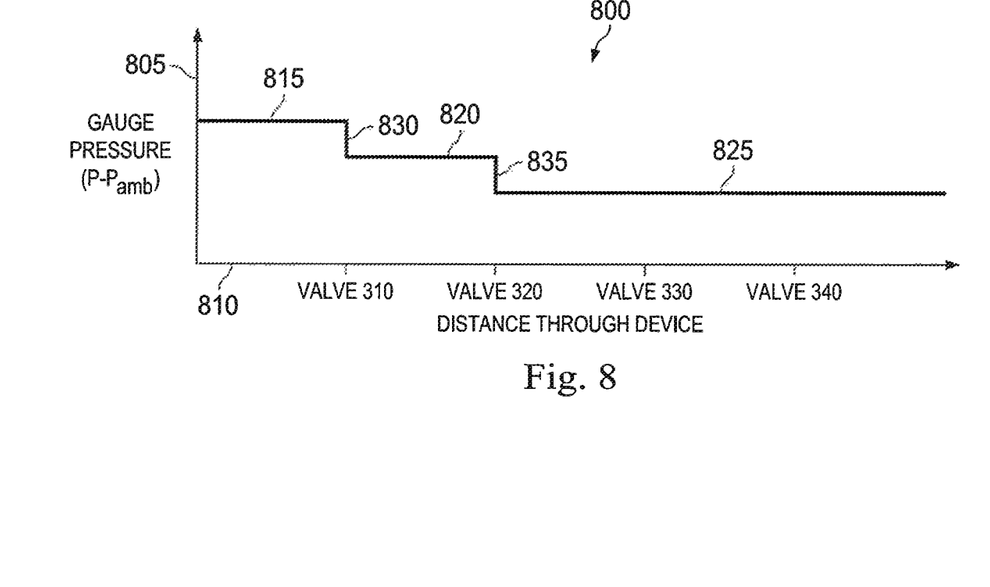
FIG. 8 is a graphical illustration of changes in gauge pressure within and along the length of the exemplary flow system as depicted in FIG. 7, where some valves are in an inactive condition and other valves are in an active condition.

FIG. 8 illustrates a graph 800 depicting the changes in gauge pressure within and along the length of the drainage device 105 in the situation shown in FIG. 7. In particular, the valves 310 and 320 are an ACTIVE condition (i.e., contributing to the pressure drop across the drainage device 105), and the valves 330 and 340 are an INACTIVE condition (i.e., not contributing to the pressure drop across the drainage device 105). The y-axis 805 of the graph in FIG. 8 reflects the gauge pressure (absolute pressure in the drainage tube 200 minus the ambient pressure), and the x-axis 810 reflects position along the length of the drainage device 105 past the valves 310, 320, 330, and 340 (i.e., the distance traveled by the fluid within the drainage device 105).

In one exemplary situation, the graph 800 depicts the pressure changes along the length of the drainage device 105 after scarring or fibrosis of a bleb has begun to occur at the drainage site 220. Because the switch elements 352 and 354 are in an ACTIVE position, the corresponding valves 310 and 320 contribute to the pressure drop across the drainage device 105. In other words, because the switch elements 352 and 354 are in an ACTIVE position, the corresponding valves 310 and 320 add to the threshold pressure necessary to overcome to allow fluid to drain through the drainage device 105. In contrast, the switch elements 356 and 358 are in an INACTIVE position, and so the corresponding valves 330 and 340 do not contribute to the pressure drop across the drainage device 105. Thus, in this scenario, the drainage device 105 has a lower pressure threshold needed to be overcome to allow fluid to flow through the drainage device 105 than in the scenario depicted in FIG. 5 (i.e., where every valve 310, 320, 330, and 340 contributes to the pressure drop across the drainage device 105).

As shown by the graph 800, the pressure within the drainage device 105 decreases in a staggered or stepwise fashion by discrete amounts reflecting the pressure drops across the series of valves 310, 320, 330, and 340. Line 815 represents the gauge pressure within the drainage device 105 proximal of the valve 310. In the pictured embodiment, line 815 reflects the pressure within the drainage device 105 at zone P1, or the anterior chamber pressure. In the pictured embodiment, line 820 reflects the pressure within the drainage device 105 between the valve 310 and the valve 320. In the pictured embodiment, line 825 reflects the pressure within the drainage device 105 distal the valve 320 (e.g., at the drainage site 220 shown in FIG. 4). As shown by FIGS. 6 and 8, the drainage site pressure after scarring of the bleb (represented by line 825 in FIG. 8) is higher than the drainage site pressure immediately after implantation of the drainage device (represented by line 635 in FIG. 6). Line 830 represents the pressure drop across the valve 310. Line 835 represents the pressure drop across the valve 320. Because the switch mechanisms of the valves 330 and 340 are in an INACTIVE condition, the valves 330 and 340 do not substantially contribute to the pressure drop across the flow system 300. Thus, the overall pressure drop across the flow system 300 in this scenario is lower than the overall pressure drop across the flow system in the scenario pictured in FIG. 6. Thus, fluid flowing from the anterior chamber through the drainage device 105 has less of a pressure threshold to overcome than in a situation where more switch elements are in an ACTIVE condition (e.g., the situation pictured in FIG. 5).

The healthcare provider may repeatedly reevaluate the anterior chamber pressure (i.e., pressure in zone P1) to assess whether aqueous humor is appropriately draining from the patient's eye. If not, the user may then readjust the pressure threshold of the flow device 300 by activating and/or deactivating any number of the switch elements 352, 354, 356, 358 to affect the rate of flow through the drainage device 105. Thus, by controlling the operation of the flow system 300, a desired pressure differential (that corresponds to a desired flow rate) across the drainage device 105 can be maintained.

Figure 9:
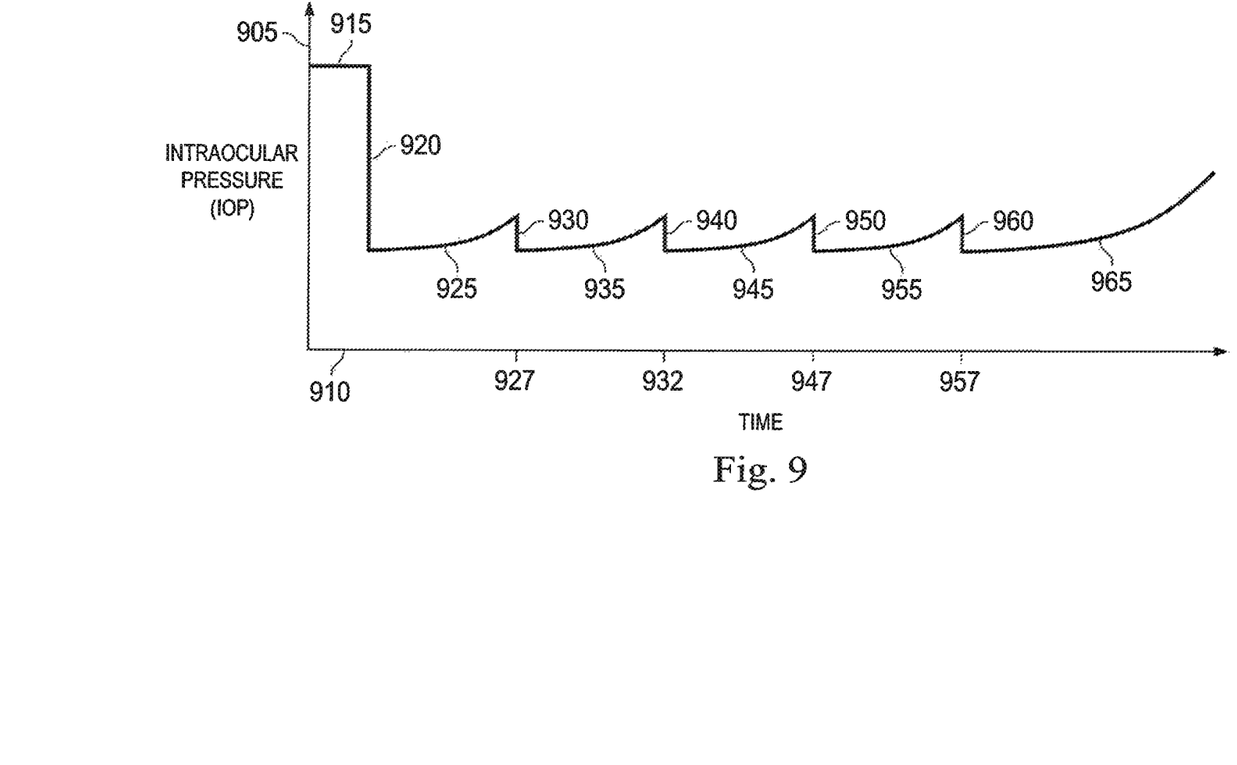
FIG. 9 is a graphical illustration of changes in intraocular pressure over time in an exemplary scenario utilizing the flow system illustrated in FIGS. 5 and 7.

FIG. 9 shows a graph 900 illustrating the changes in IOP or intraocular pressure over time in an exemplary treatment situation where a user selectively deactivates individual valves at discrete intervals. The y-axis 905 of the graph in FIG. 8 reflects the IOP (pressure in the anterior chamber, i.e., zone P1), and the x-axis 910 reflects time elapsed since implantation of the drainage device 105 in the eye of the patient. In the pictured embodiment, all the valves 310, 320, 330, and 340 in the drainage device 105 are in an ACTIVE condition upon implantation of the drainage device. Line 915 reflects the initial IOP in the patient's anterior chamber before implantation of the drainage device. Line 920 reflects the immediate drop in IOP that occurs upon implantation of the drainage device 105 within the patient's eye. After the initial drop in IOP depicted by line 920, the IOP may gradually rise due to faulty drainage as a result of scarring at the drainage site (i.e., scarring or fibrosis of the bleb). The increase in drainage site pressure hinders the passive flow of fluid through the drainage device 105, which causes the gradual increase in IOP reflected by line 925.

In the pictured embodiment, a user (e.g., a healthcare provider) may measure the IOP before a time 927 and observe this upswing in IOP. In order to compensate for the increase in drainage site pressure and alleviate the increase in IOP, the user may deactivate one or more valves within the drainage device 105. In one example, the user initially deactivates one valve. In this embodiment, for example, the user deactivates valve 310 at time 927. Deactivation of the valve 310 minimizes the contribution of valve 310 to the overall pressure drop across the drainage device 105, and lessens the pressure threshold needed to be overcome to allow passive fluid flow through the drainage device 105. Thus, the passive fluid flow through the drainage device 105 increases, and, consequently, the IOP drops, as reflected by line 930.

In the pictured embodiment, the graph 900 depicts a cycle of IOP increase due to progressive scarring of the bleb (i.e., at the drainage site 220 shown in FIG. 4) and IOP decrease due to selective valve deactivation. For example, line 935 reflects the gradual rise of IOP as the bleb continues to scar or fibrose. The user may measure the IOP before a time 932 and observe this increase in IOP. In order to alleviate the increase in IOP due to bleb failure, the user may deactivate one or more valves within the drainage device 105. Line 940 reflects the immediate drop in IOP that occurs upon deactivation of one of the remaining valves 320, 330, 340 in the drainage device 105 within the patient's eye. For example, in the pictured embodiment, the user deactivates valve 320 at time 932. Deactivation of the valve 320 minimizes the contribution of valve 320 to the overall pressure drop across the drainage device 105, and lessens the pressure threshold needed to be overcome to allow passive fluid flow through the drainage device 105. Thus, as the passive fluid flow increases through the drainage device 105, the resultant IOP drop is reflected by line 940.

Similarly, line 945 reflects the gradual rise of IOP as the bleb continues to scar or fibrose. The user may measure the IOP before a time 947 and observe this increase in IOP. In order to alleviate the increase in IOP due to bleb failure, the user may deactivate one or more remaining valves within the drainage device 105. Line 950 reflects the immediate drop in IOP that occurs upon deactivation of one of the remaining valves 330, 340 in the drainage device 105 within the patient's eye. For example, in the pictured embodiment, the user deactivates valve 330 at time 947. Deactivation of the valve 330 minimizes the contribution of valve 330 to the overall pressure drop across the drainage device 105, and lessens the pressure threshold needed to be overcome to allow passive fluid flow through the drainage device 105. Thus, as the passive fluid flow increases through the drainage device 105, the resultant IOP drop is reflected by line 950.

Similarly, line 955 reflects the gradual rise of IOP as the bleb continues to scar or fibrose. The user may measure the IOP before a time 957 and observe this increase in IOP. In order to alleviate the increase in IOP due to bleb failure, the user may deactivate one or more remaining valves within the drainage device 105. Line 960 reflects the immediate drop in IOP that occurs upon deactivation of the remaining valve 340 in the drainage device 105 within the patient's eye. For example, in the pictured embodiment, the user deactivates valve 340 at time 957. Deactivation of the valve 340 minimizes the contribution of valve 340 to the overall pressure drop across the drainage device 105, and lessens the pressure threshold needed to be overcome to allow passive fluid flow through the drainage device 105. Thus, as the passive fluid flow increases through the drainage device 105, the resultant IOP drop is reflected by line 960.

Once every valve within the drainage device has been deactivated, and the drainage device 105 allow substantially free flow of fluid through the drainage tube 200 (shown in FIG. 4), the IOP may continue to gradually increase as the scarring or fibrosis of the bleb continues to progress. This gradual increase in IOP is reflected by line 965.

The devices, systems, and methods described herein achieve IOP control with a relatively small and less expensive device than other implants typically used for IOP control. Due to the simplicity of the design of the flow systems disclosed herein, the overall size of the implant may be dramatically reduced, allowing for implantation in confined areas such as the suprachoroidal space. The embodiments of the IOP control system disclosed herein accomplish this using moveable switch elements and flexible membranes to affect drainage flow. Other embodiments may include any of a variety of flow-regulating elements that can be selectively actuated between ACTIVE and INACTIVE conditions as described above. While generally described with the valves 310, 320, 330, and 340 having an open and closed condition, it is understood that the valve conditions may be opened by varying degrees and the system may operate to control each valve by opening and closing one or more valves to a greater or lesser amount as described to control the flow through the flow system 205.

The exemplary system disclosed herein allows the user to take into account intraocular pressures, bleb pressures, and/or the post-operative time lapse in regulating drainage flow. The IOP control system disclosed herein may work to extend the longevity of the drainage device by allowing a user to lower the pressure differential threshold of the flow system in a stepwise fashion, thereby enabling the device to remain effective at controlling IOP for a longer period of time as the pressure increases at the drainage site (e.g., secondary to bleb scarring or fibrosis). In addition, the exemplary IOP control system disclosed herein does not require a continuous power supply to maintain such adjustments in valve properties, and the adjustments may be done remotely without the need for additional surgery.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An TOP control device for implantation in an eye of a patient, comprising:
   a housing sized for implantation into the eye of the patient and including an inlet port and an outlet port;
   a fluid flow passageway extending from the inlet port to the outlet port, the fluid flow passageway being configured to allow the flow of fluid from the inlet port to the outlet port; and
   at least one valve disposed within the housing, the at least one valve including a first side and an opposing second side, the at least one valve comprising a switch element movable to a first position and a second position relative to the housing, the first position placing the valve in the active condition and the second position placing the valve in the inactive condition wherein the first position positions the switch element away from an inner surface of the housing into the fluid flow passageway, and the second position positions the switch element against the inner surface of the housing, the at least one valve configured to affect flow through the fluid flow passageway from the inlet port to the outlet port by moving in response to pressure differentials acting on the opposing first and second sides, the at least one valve being remotely adjustable between an active condition increasing resistance to the flow of fluid within the fluid flow passageway and an inactive condition decreasing resistance to the flow of fluid within the fluid flow passageway.

2. The TOP control device of claim 1, wherein the at least one valve comprises a sealing portion being shaped and configured to control flow rates of aqueous humor through the fluid flow passageway by deflecting in response to pressure differentials acting across the sealing portion.

3. The TOP control device of claim 2, wherein the sealing portion comprises a flexible membrane responsive to a pressure differential across a first membrane surface and an opposing second membrane surface.

4. The TOP control device of claim 2, wherein the sealing portion comprises a flexible, corrugated membrane.

5. The TOP control device of claim 2, wherein the switch element couples the sealing portion to the housing.

6. An TOP control system, comprising:
a drainage device sized for implantation in an eye of a patient, comprising:
a drainage tube including a proximal end and a distal end, and a lumen extending therebetween;
a flow system in communication with the lumen of the drainage tube, the flow system comprising:
a housing including an inlet port and an outlet port;
a fluid flow passageway extending from the inlet port to the outlet port, the fluid flow passageway being configured to allow the flow of fluid from the inlet port to the outlet port; and
a first valve disposed within the housing and configured to have a first cracking pressure, the first valve including a first side, and an opposing second side, the first valve configured to affect flow through the fluid flow passageway by deflecting in response to pressure differentials acting on the opposing first and second sides;
a second valve configured to have a second cracking pressure; and
an external control device being operable to selectively and remotely control the first valve to assume an active condition wherein the first valve increases resistance to the flow of fluid within the fluid flow passageway and to assume an inactive condition wherein the first valve decreases resistance to the flow of fluid within the fluid flow passageway; and further wherein the external control device comprises an actuator configured to selectively activate or deactivate the second valve.

7. The TOP control system of claim 6, wherein the first valve comprises a switch element coupling a sealing portion to the housing.

8. The TOP control system of claim 7, wherein the sealing portion is shaped and configured to control flow rates of aqueous humor through the fluid flow passageway by deflecting in response to pressure differentials acting across the sealing portion.

9. The TOP control system of claim 8, wherein the sealing portion comprises a flexible membrane responsive to a pressure differential across a first membrane surface and an opposing second membrane surface.

10. The TOP control system of claim 7, wherein the switch element is movable to a first position and a second position relative to the housing, the first position placing the first valve in the active condition and the second position placing the first valve in the inactive condition.

11. The TOP control system of claim 10, wherein the first position positions the switch element away from an inner surface of the housing into the fluid flow passageway, and the second position positions the switch element and the sealing portion against the inner surface of the housing.

12. The TOP control system of claim 10, wherein the external control device comprises an actuator configured to selectively activate the first valve by moving the switch element to the first position.

13. The IOP control system of claim 10, wherein the external control device comprises an actuator configured to selectively deactivate the first valve by moving the switch element to the second position.

14. The TOP control system of claim 6, wherein the first cracking pressure and the second cracking pressure are the same.

15. The TOP control system of claim 14, wherein the first cracking pressure and the second cracking pressure are different.

* * * * *